United States Patent [19]
Hardt

[11] Patent Number: 6,059,744
[45] Date of Patent: May 9, 2000

[54] ANKLE SUPPORT AND HEEL CUSHIONING DEVICE

[75] Inventor: John C. Hardt, Belton, Tex.

[73] Assignee: Spenco Medical Corporation, Waco, Tex.

[21] Appl. No.: 09/179,433

[22] Filed: Oct. 27, 1998

[51] Int. Cl.[7] .................................................. A61F 13/00
[52] U.S. Cl. ................................. 602/62; 602/65; 602/27
[58] Field of Search .............................. 602/20, 62, 63, 602/65, 23, 27–29; 362/89, 92, 113–115, 24.5, 28.37

[56] References Cited

U.S. PATENT DOCUMENTS

| | | | |
|---|---|---|---|
| 3,028,861 | 4/1962 | Shapiro | 128/166 |
| 4,084,586 | 4/1978 | Hettick | 128/157 |
| 4,166,460 | 9/1979 | Applegate | 128/80 |
| 4,179,826 | 12/1979 | Davidson | 36/69 |
| 4,928,404 | 5/1990 | Scheuermann | 36/37 |
| 4,974,343 | 12/1990 | Davidson | 36/89 |
| 5,197,942 | 3/1993 | Brady | 602/5 |
| 5,472,414 | 12/1995 | Detty | 602/27 |

FOREIGN PATENT DOCUMENTS

WO9221257  12/1992  WIPO .............................. A43B 7/32

*Primary Examiner*—Richard J. Apley
*Assistant Examiner*—J Saydah
*Attorney, Agent, or Firm*—Sidley & Austin

[57] ABSTRACT

A unitary ankle supporting and heel cushioning device being an ankle strap attached to a heel cushioning portion which can be worn with or without a shoe. The device allows a portion of the foot to be exposed which allows for activities to be performed which require the grip of a bare foot. The heel cushioning portion may also include a heel plug to provide additional heel cushioning.

13 Claims, 2 Drawing Sheets

ANKLE SUPPORT AND HEEL CUSHIONING DEVICE

TECHNICAL FIELD

The present invention relates to a heel cushioning device and more particularly to a device which provides both an ankle support and heel cushioning properties.

BACKGROUND OF THE INVENTION

There are various devices that have been developed to stabilize the foot and relieve stress on the foot. U.S. Pat. No. 4,084,586 describes an elastic, shaped foot support with a heel opening. The device described in '586 does not, however, provide any means for heel cushioning. Other existing elastic supports do not have heel openings but are designed as cushioned tubes which may be pulled over the foot and which extend from the plantar surface to the ankle when worn.

Various heel cushioning devices have also been manufactured and used. These are primarily designed to be placed inside a shoe of the wearer. While providing cushioning for the heel, these devices do not provide any ankle support. One such device is sold by Spenco Medical Corporation under the trademark POLYSORB and has a body defining a cup-like recess to receive the heel of the wearer's foot.

In order to obtain both ankle support and heel cushioning or support, various approaches have been tried. For example, some have attempted to use separate elastic supports for the foot simultaneously with a heel support. This has not provided a satisfactory result due to the bulk of this combination which makes it unsuitable for wearing a shoe or boot. However, since a heel cup has no means of attachment to the foot, it was necessary to use a shoe or boot if the heel cup was to be used. In other devices, the heel cup has been secured to an elastic device, but this has not solved the bulk problem.

More specifically, many athletes are in need of an ankle supporting and heel cushioning device which can be used with or without a shoe. For example, dancers put an enormous amount of stress on their ankles and heels. While rehearsing, they may need additional support while barefoot. During a performance, they would wear dance shoes. There is a need for a device which can accommodate both situations. Gymnasts practice and perform in bare feet, but are often in need of extra ankle support and heel cushioning due to the enormous stress and impact of vaults and dismounts. In addition, the device must allow enough of the bare foot to be exposed so that the gymnast can maintain contact with the floor so as not to slip. Skaters often practice their choreography on land before moving to the ice. They need a device which can be used while practicing jumps on the floor and then be utilized in a skate for movements on the ice.

While the aforementioned devices have been reported, there is still a need for a device which both supports the ankle and cushions the heel without presenting multiple layers to the foot and shoe, and which can be used both in a shoe and on a bare foot, and which allows for exposure of the ball of the foot for gripping of the floor in certain athletic activities.

SUMMARY OF THE INVENTION

A device has now been invented which provides improved ankle supporting and heel cushioning properties without adding the bulk of multiple layers. Such a device can be worn with or without a shoe, boot, roller blade, ice skate, dance shoe, or other foot outerwear. In another embodiment, the device allows a significant portion of the bare foot to be exposed which allows for activities to be performed which require the grip of a bare foot.

In a preferred embodiment, the invention is a unitary ankle supporting and heel cushioning device comprising an ankle strap attached to a heel cup. The heel cup may have a heel plug to provide additional heel cushioning.

DETAILED DESCRIPTION OF THE INVENTION

Figure 1:
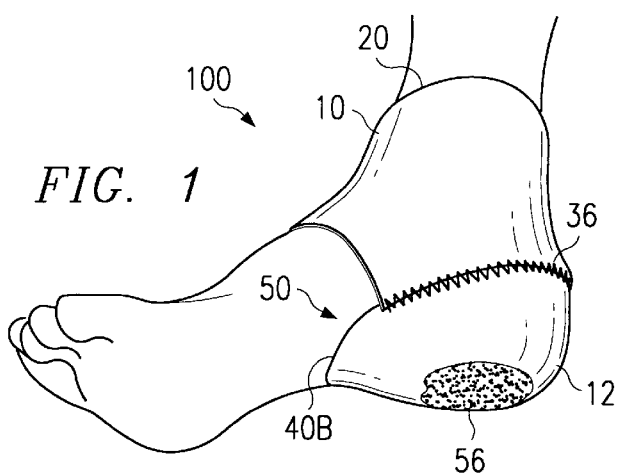
FIG. 1 is a isometric view of the heel cup and ankle strap sewn together according to the present invention.
Figure 2:
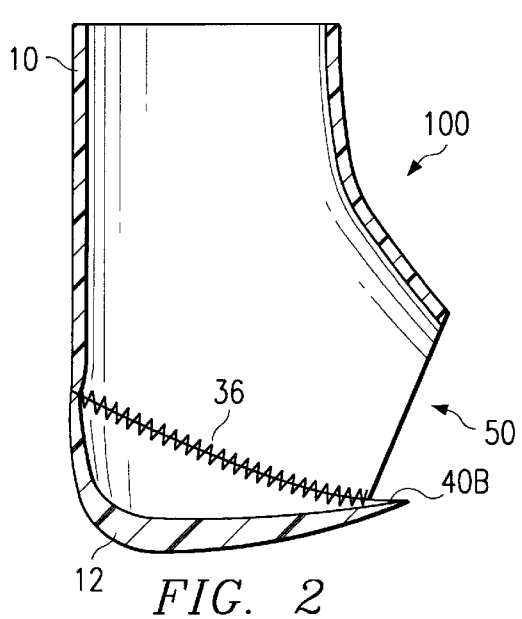
FIG. 2 is an isometric view of the heel cup and ankle strap sewn together according to the present invention.
Figure 4:
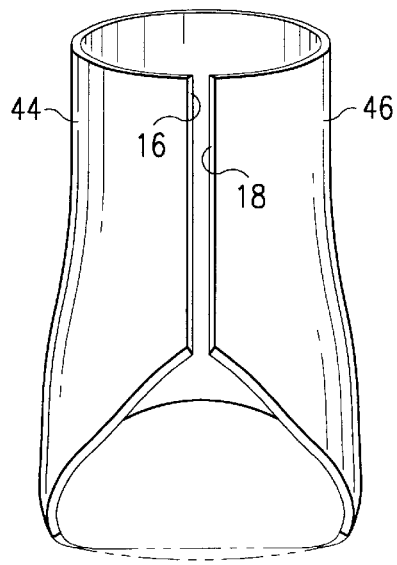
FIG. 4 illustrating the fabrication of the anklet prior to the attachment of the heel cushion.
Figure 3:
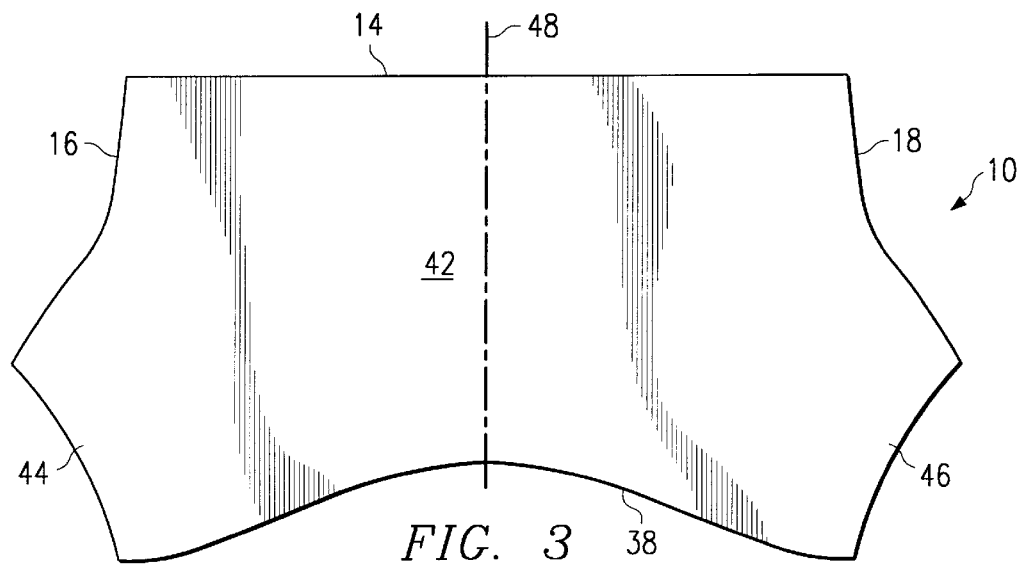
FIG. 3 is a plan view of the ankle strap in a flattened condition prior to assembly.

The present invention relates to an ankle supporting and heel cushioning device the preferred embodiment of which is shown in FIGS. 1 and 2 and is generally designated by the numeral 100. The ankle support and heel cushioning device is designed to support the ankle and absorb shock in the heel area and includes an ankle strap 10 and a shock absorbing heel cup 12. The ankle strap may be formed as one piece or fabricated in a sewing operation. Referring to FIGS. 3 and 4, the fabrication and assembly of the support and cushioning device is shown.

Ankle strap 10 has top edge 14 and two upper side edges, 16 and 18. Ankle strap 10 defines an interior opening 20 which receives the foot and ankle of the wearer. The top edge 14 of the ankle strap preferably extends to an area at least above the ankle bone of the wearer. The ankle strap is preferably constructed from a stretchable material such as neoprene of the type commonly used in such applications as diver's wetsuits or an elastic type of material such as natural latex rubber or elastic bandage. The material of fabrication of the ankle strap may vary but the material used should be sufficiently elastic to provide suitable support.

Figure 5:
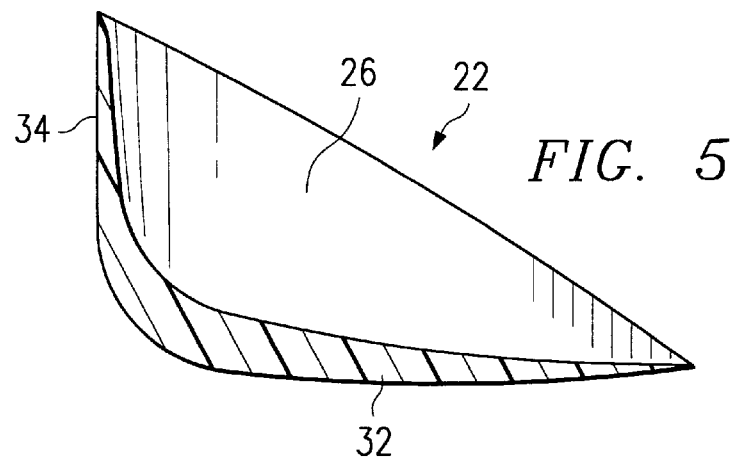
FIG. 5 is a cross sectional view of the heel cup according to the present invention.
Figure 6:
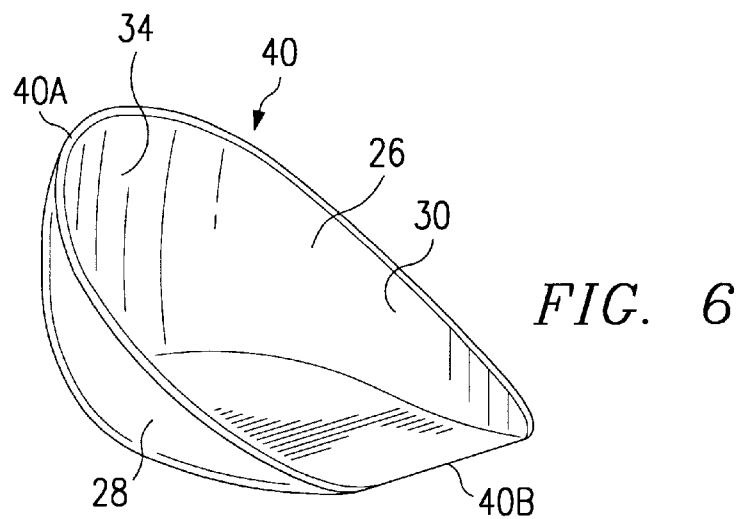
FIG. 6 is an isometric view of the heel cup according to the prevent invention.

The heel cushioning portion prior to assembly is shown in FIGS. 5 and 6. The heel cushioning portion 22 defines a cup-like body. The cup-like body has an interior heel-receiving cavity 26 defined by opposite side walls 28 and 30, platform 32 and generally vertical rear wall 34. Preferably the heel cup is molded as an integral unit from light weight material such as polyurethane or any other open cell foam material. Other rubber and vinyl compounds can also be used.

The heel cushioning portion 22 is attached to the ankle strap 10 at bottom edge 38 by any appropriate means. Preferably, it is attached by bonding, by using an adhesive or by sewing as shown with a seam 36 extending about the top edge 40 of the heel cup. Top edge 40 has two portions: a first top edge portion 40A and a second top edge portion 40B.

The ankle strap 10 may be formed as a one piece unit or fabricated by sewing. Referring to FIGS. 3 and 4, the fabrication and assembly of the ankle support and heel cushioning portion is shown. Numeral 42 demonstrates a piece of material which forms the ankle strap 10 which has been cut in the preferred shape. Piece of material 42 has a left hand section designated by numeral 44 and a right hand section designated by numeral 46. FIG. 3 demonstrates the piece of material with the inner side positioned towards the viewer. The ankle strap 10 is assembled as illustrated in FIG. 4 with left hand section 44 and right hand section 46 being folded about fold line 48. The two upper side edges, 16 and 18, are joined by bonding, an adhesive, or sewing. Heel cushioning portion 22 may then be attached along bottom edge 38 by bonding, an adhesive, or by sewing as shown with a seam 36 extending about the first top edge portion 40A of top edge 40 of the heel cushioning portion.

In use, the wearer inserts his foot into opening 20 of the ankle strap 10. The upper edge 14 is grasped and pulled upwardly. The foot is now positioned so that the ankle strap is securely about the ankle and the wearer's heel is in the heel cup. A portion of the wearer's foot may extend from the front edge 50.

Figure 7:
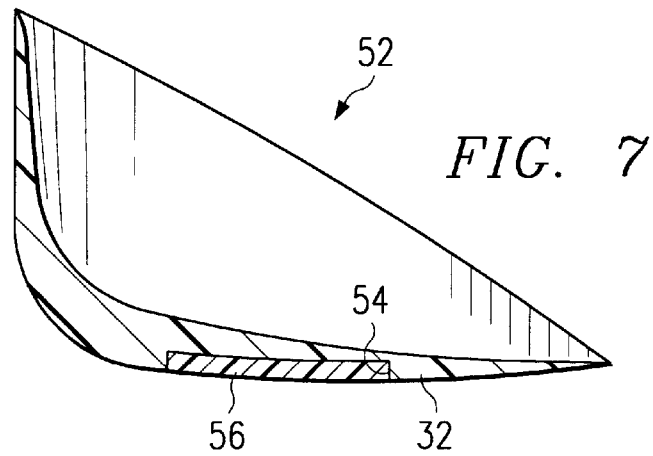
FIG. 7 is a cross section view of the heel cup with a cavity to receive a heel plug according to the present invention.

FIG. 7 illustrates another embodiment of the present invention which is illustrated as numeral 52. In this embodiment, the heel cup is formed generally as shown in FIGS. 6 and 7. The platform 32 of the heel cup defines a cavity 54 containing a heel plug. The heel plug provides an additional shock absorbing and cushioning effect to the heel. The desired material for the heel plug 56 is material which provides cushion and durability such as neoprene. Any other type of closed or open cell foam may also be used. Ankle strap 10 is constructed and attached in the same manner as discussed above.

It will be found that the present invention provides a new unitary ankle supporting and heel cushioning device which does not add the layers and bulk of other devices. The wearer of the present invention benefits from added ankle support and heel cushioning without the problems caused by multiple layers which include discomfort, improper shoe fitting, and the need to purchase special shoes to accommodate bulky devices. Further, the unitary nature of the device provides an advantage over wearing a separate ankle support with a heel cup. Because separate heel cups have no means of attachment to the foot, they are designed to be worn with a shoe. If the separate ankle support and heel cup are too bulky to fit within a shoe, the combination is not usable. The present invention can be worn with or without a shoe. In addition, the present invention allows for a large part of the foot's plantar surface to be exposed allowing the wearer to use the invention for activities which require the grip of a bare foot.

It will be apparent to those skilled in the art to make various changes, alterations, and modifications to the present invention. To the extent that these changes, alterations, and modifications do not depart from the spirit and scope of the appended claims, they are intended to be encompassed therein.

I claim:

1. An ankle supporting and heel cushioning device for a foot comprising:

(a) an ankle strap defining a foot receiving opening for receiving a portion of a foot of a wearer, a front edge and a bottom edge wherein said bottom edge forms a heel-receiving opening;

(b) a heel cushioning portion having a first top edge portion and a second top edge portion, said heel cushioning portion defining a heel-receiving cavity, said heel cushioning portion attached to said ankle strap at an attachment zone formed by said bottom edge of said ankle strap and said first top edge portion of said heel cushioning portion.

2. The device of claim 1, wherein said front edge of said ankle strap and said second top edge portion of said heel cushioning portion define a second opening which permits extension therethrough of a portion of a wearer's foot.

3. The device of claim 1 wherein said heel cushioning portion has an interior and an exterior surface and wherein said exterior surface defines a recess further comprising a shock absorbing component secured in said recess.

4. The device of claim 3 wherein said shock absorbing material comprises a closed or open cell foam material.

5. An ankle supporting and heel cushioning device for the foot comprising:

(a) an ankle strap defining a foot-receiving opening for receiving a portion of a foot of a wearer, said ankle strap having a bottom edge wherein said bottom edge forms a heel-receiving opening, said ankle strap comprising an elastic material; and (b) a heel cushioning portion having a first top edge portion and a second top edge portion, said heel cushioning portion defining a heel-receiving cavity, said heel cushioning portion attached to said ankle strap at an attachment zone formed by said bottom edge of said ankle strap and said first top edge portion of said heel cushioning portion, wherein said heel cushioning portion has an interior and an exterior surface, said exterior surface defining a recess, said heel cushioning portion further comprising a shock absorbing component secured in said recess.

6. The device of claim 5 wherein said elastic material is neoprene.

7. The device of claim 5 wherein said shock absorbing component comprises a neoprene material.

8. The device of claim 5 wherein said heel cup comprises a polyurethane material.

9. The device of claim 6 wherein said heel cup comprises a polyurethane material.

10. The device of claim 7 wherein said heel cup comprises a polyurethane material.

11. The device of claim 5 wherein said heel cushioning portion is adapted to contact a portion of the plantar surface of the wearer's foot during wear so that the ball of said wearer's foot is exposed.

12. The device of claim 2 wherein said heel cushioning portion has an interior and an exterior surface and wherein said exterior surface defines a recess further comprising a shock absorbing component secured in said recess.

13. The device of claim 12 wherein said shock absorbing component comprises a closed or open cell foam material.

* * * * *

UNITED STATES PATENT AND TRADEMARK OFFICE
CERTIFICATE OF CORRECTION

PATENT NO. : 6,059,744
DATED : May 9, 2000
INVENTOR(S) : John C. Hardt

It is certified that error appears in the above-identified patent and that said Letters Patent is hereby corrected as shown below:

Column 1, line 32, after "wearing" insert --with--.

Column 2, line 19, change "illustrating" to "is an illustration of".

Column 2, line 24, change "prevent" to "present".

Column 2, line 25, change "section" to "sectional".

Column 2, line 37, change "FIGS. 3 and 4" to "FIGS. 2, 3 and 4".

Column 2, line 48, change "diver's" to "divers'".

UNITED STATES PATENT AND TRADEMARK OFFICE
CERTIFICATE OF CORRECTION

PATENT NO. : 6,059,744
DATED : May 9, 2000
INVENTOR(S) : John C. Hardt It is certified that error appears in the above-identified patent and that said Letters Patent is hereby corrected as shown below:

Column 2, line 57, change "light weight" to "lightweight".

Column 3, line 2, change "FIGS. 3 and 4" to "FIGS. 2, 3 and 4".

Column 3, line 13, before "sewing" insert --by--.

Column 3, line 15, after "sewing" insert --,--.

Column 3, line 18, change "the wearer inserts his foot" to "the wearer's foot is inserted".

Column 3, line 30, before "material" insert --a--.

Signed and Sealed this

Twentieth Day of February, 2001

Attest:

NICHOLAS P. GODICI

*Attesting Officer*   *Acting Director of the United States Patent and Trademark Office*